(12) United States Patent
Aoki

(10) Patent No.: US 9,568,395 B2
(45) Date of Patent: Feb. 14, 2017

(54) NOX SENSOR CONTROL DEVICE

(75) Inventor: Keiichiro Aoki, Shizuoka-ken (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 301 days.

(21) Appl. No.: 14/374,019

(22) PCT Filed: Feb. 15, 2012

(86) PCT No.: PCT/JP2012/053519
§ 371 (c)(1),
(2), (4) Date: Jul. 23, 2014

(87) PCT Pub. No.: WO2013/121534
PCT Pub. Date: Aug. 22, 2013

(65) Prior Publication Data
US 2015/0013441 A1     Jan. 15, 2015

(51) Int. Cl.
*G01M 15/10* (2006.01)
*G01N 27/406* (2006.01)
*G01N 33/00* (2006.01)
*G01K 3/00* (2006.01)
*G01N 27/02* (2006.01)

(52) U.S. Cl.
CPC .............. *G01M 15/102* (2013.01); *G01K 3/00* (2013.01); *G01N 27/02* (2013.01); *G01N 27/4065* (2013.01); *G01N 33/0037* (2013.01)

(58) Field of Classification Search
CPC ... G01N 33/0037; G01N 27/02; F02D 41/146; G01K 3/00; G01M 15/102
USPC ...................................................... 73/114.71
See application file for complete search history.

(56) References Cited

U.S. PATENT DOCUMENTS

| | | | | |
|---|---|---|---|---|
| 6,164,125 | A * | 12/2000 | Kawase | G01N 27/4175 60/277 |
| 6,996,499 | B2 * | 2/2006 | Kurokawa | G01N 27/4175 204/401 |
| 7,445,698 | B2 * | 11/2008 | Hada | G01N 27/4071 204/401 |
| 7,671,600 | B2 * | 3/2010 | Suzuki | G01N 27/407 324/465 |

(Continued)

FOREIGN PATENT DOCUMENTS

| | | |
|---|---|---|
| JP | H08128979 A | 5/1996 |
| JP | 2000-227364 A | 8/2000 |

(Continued)

*Primary Examiner* — Freddie Kirkland, III
(74) *Attorney, Agent, or Firm* — Dinsmore & Shohl LLP

(57) ABSTRACT

For a predetermined period prior to detecting sensor output of a single-cell type NOx sensor, a state is induced in which a voltage is not applied between a pair of electrodes or a state in which a potential difference between the electrodes is less than a reference value. The "reference value" for the potential difference between the electrodes can be appropriately set within a range that is at least less than the aforementioned voltage for detecting the output, and is 0 V or a small potential difference in the vicinity of 0 V. Thus, a certain amount of NOx is caused to accumulate on the electrodes of the NOx sensor. After the predetermined period has elapsed, a voltage for sensor output detection is applied between the electrodes. The NOx concentration is detected according to the sensor output at a time that the voltage for sensor output detection is applied.

20 Claims, 10 Drawing Sheets

(56) References Cited

U.S. PATENT DOCUMENTS

| | | | |
|---|---|---|---|
| 7,776,194 B2* | 8/2010 | Kawase | G01N 27/4175 |
| | | | 204/424 |
| 8,092,663 B2* | 1/2012 | Hada | G01N 27/4065 |
| | | | 204/406 |
| 2003/0164023 A1 | 9/2003 | Gruenwald et al. | |
| 2004/0153258 A1 | 8/2004 | Kurokawa et al. | |
| 2004/0217001 A1* | 11/2004 | Hada | G01N 27/4071 |
| | | | 204/424 |
| 2009/0205957 A1* | 8/2009 | Hada | G01N 27/4065 |
| | | | 204/406 |
| 2009/0218220 A1 | 9/2009 | Matter et al. | |

FOREIGN PATENT DOCUMENTS

| | | |
|---|---|---|
| JP | 2004-144733 A | 5/2004 |
| JP | 2004-519694 A | 7/2004 |
| JP | 2007-256232 A | 10/2007 |
| JP | 2008-304383 A | 12/2008 |
| JP | 2009-222708 A | 10/2009 |
| JP | 2010-249540 A | 11/2010 |
| JP | 2011-513735 A | 4/2011 |

* cited by examiner

FIG. 7

| UPSTREAM | SENSOR CURRENT [mA] | 0.1 | 0.2 | 0.3 | 0.4 | 0.5 | 0.6 |
|---|---|---|---|---|---|---|---|
| | NOx CONCENTRATION [ppm] | 100 | 200 | 300 | 400 | 500 | 600 |

| DOWNSTREAM | SENSOR CURRENT [mA] | 0.1 | 0.2 | 0.3 | 0.4 | 0.5 | 0.6 |
|---|---|---|---|---|---|---|---|
| | NOx CONCENTRATION [ppm] | 10 | 20 | 30 | 40 | 50 | 60 |

NOX SENSOR CONTROL DEVICE

TECHNICAL FIELD

The present invention relates to a NOx sensor control device. More particularly, the present invention relates to a single-cell type NOx sensor control device that includes a pair of electrodes disposed on two sides of a solid electrolyte.

BACKGROUND ART

A single-cell type NOx sensor that includes a pair of electrodes on two sides of a solid electrolyte is disclosed in Patent Literature 1. A perovskite-type electrode is used as a detection electrode in the aforementioned NOx sensor. A perovskite-type electrode has selective absorptivity with respect to NOx. The aforementioned NOx sensor adopts a decomposition current that flows when NOx that was adsorbed on the detection electrode is decomposed as an output. The decomposition current has a correlation with the NOx concentration, and therefore the NOx concentration is detected by detecting the decomposition current.

CITATION LIST

Patent Literature

Patent Literature 1: National Publication of International Patent Application No. 2011-513735
Patent Literature 2: Japanese Patent Laid-Open No. 08-128979
Patent Literature 3: Japanese Patent Laid-Open No. 2007-256232

SUMMARY OF INVENTION

Technical Problem

When using a NOx sensor that uses perovskite-type electrodes as described in the aforementioned Patent Literature 1, a large amount of NOx is absorbed on the detection electrode under an environment in which there is a high NOx concentration, and the detected decomposition current is also large. Therefore, the NOx concentration can be detected with a comparatively high accuracy. On the other hand, the rate of NOx adsorption on the detection electrode decreases under an environment in which the NOx concentration is extremely low. In this case, even if a perovskite-type electrode is used as a detection electrode and the electrode surface area is enlarged, the decomposition current will still be an extremely small current. Consequently, it is considered that under an environment in which there is a low NOx concentration, errors and fluctuations in the sensor output are liable to increase, and in some cases it is difficult to detect the NOx concentration within the range of a required low concentration.

Further, it is considered that even if a very small trace amount of the decomposition current is detected, it is necessary to provide, for example, a device that performs processing to amplify the signal or eliminate noise or the like in order to detect the NOx concentration at a control device based on an output signal which has a small current value.

An object of the present invention is to solve the above described problem, and the present invention provides a NOx sensor control device that is improved so that the detection accuracy with respect to a NOx concentration of a NOx sensor can be improved while suppressing an increase in the equipment required for NOx detection.

Solution to Problem

To achieve the above described object, the present invention relates to a NOx sensor control device that controls a NOx sensor that is disposed in an exhaust passage of an internal combustion engine, in which the NOx sensor includes a solid electrolyte and a pair of electrodes that are disposed so as to sandwich the solid electrolyte, and emits a sensor output that depends on a NOx concentration of a gas that is a detection object. The NOx sensor control device of the present invention includes means for inducing, for a predetermined period prior to detection of the sensor output, a state in which a voltage is not applied between the pair of electrodes or a state in which a potential difference between the pair of electrodes is less than a reference value.

Here, the "reference value" for the potential difference between the pair of electrodes can be appropriately set within a range that is at least less than a voltage for output detection that is described later, and it is desirable that the reference value is 0 V or a small potential difference in the vicinity of 0 V. Further, the "predetermined period" may be a fixed time period that is determined by taking into consideration the responsiveness required for the NOx sensor, for example, a period that is set during control in accordance with the operating state of the internal combustion engine. In a case where the NOx sensor control device of the present invention controls two or more NOx sensors, respectively, a configuration may be adopted in which the "predetermined period" can be set for each of the NOx sensors.

The NOx sensor control device of the present invention further includes means for applying a voltage for sensor output detection between the pair of electrodes after the predetermined period elapses, and means for detecting a NOx concentration in accordance with the sensor output at a time that the voltage for sensor output detection is applied.

Here, the voltage for sensor output detection may be an alternating voltage. In such a case, a frequency between 0.1 Hz and 10 Hz is more preferable as the frequency of the alternating voltage. Further, the alternating voltage may be applied for only one cycle.

The NOx sensor control device of the present invention may be a device that, after applying the voltage for sensor output detection, applies a voltage that is in an opposite direction to the voltage for sensor output detection and also is of a size that is less than or equal to the voltage for sensor output detection.

The NOx sensor control device of the present invention may further include means for setting at least one condition, in accordance with an operating state of the internal combustion engine, among a length of the predetermined period, a maximum value of the voltage for sensor output detection, and an application time period of the voltage for sensor output detection. In this case, the means for detecting a NOx concentration may detect a NOx concentration in accordance with the sensor output based on a relation between the sensor output and a NOx concentration in accordance with a preset condition.

The NOx sensor control device of the present invention may be a control device that controls each of two NOx sensors that are a first NOx sensor disposed upstream of a urea SCR catalyst in the exhaust passage of the internal combustion engine and a second NOx sensor disposed downstream of the urea SCR catalyst.

In this case, for example, a length of the predetermined period with respect to the first NOx sensor can be made shorter than a length of the predetermined period with respect to the second NOx sensor. Further, for example, a maximum value of the voltage for sensor output detection with respect to the first NOx sensor can be made less than a maximum value of the voltage for sensor output detection with respect to the second NOx sensor. Alternatively, an application time period of the voltage for sensor output detection with respect to the first NOx sensor may be shorter than an application time period of the voltage for sensor output detection with respect to the second NOx sensor.

The NOx sensor control device of the present invention may further include: means for applying, after application of the voltage for sensor output detection, an alternating voltage for which a maximum value is smaller than a maximum value of the voltage for sensor output detection; means for detecting an impedance of the solid electrolyte at a time that the small alternating voltage is applied; and means for detecting a temperature of a sensor element of the NOx sensor in accordance with the impedance.

In addition, the NOx sensor control device of the present invention may further include means for applying an alternating voltage for NOx removal between the pair of electrodes at fixed intervals to remove NOx that is present on the pair of electrodes during a period until a sensor element of the NOx sensor reaches an activation temperature.

In this case, the NOx sensor control device of the present invention may further include: means for applying, after application of the alternating voltage for NOx removal, an alternating voltage for which a maximum value is smaller than a maximum value of the alternating voltage for NOx removal; means for detecting an impedance of the solid electrolyte at a time that the small alternating voltage is applied; and means for detecting a temperature of the sensor element in accordance with the impedance.

The NOx sensor control device of the present invention may further include means for applying a direct-current voltage between the pair of electrodes during a period until a sensor element of the NOx sensor reaches an activation temperature.

In this case, the NOx sensor control device of the present invention may further include: means for superimposing an alternating voltage for impedance detection on the direct-current voltage and applying the superimposed voltage between the pair of electrodes at fixed intervals during a period until the sensor element reaches an activation temperature; means for detecting an impedance of the solid electrolyte at a time that the alternating voltage for impedance detection is applied; and means for detecting a temperature of the sensor element in accordance with the impedance.

Advantageous Effects of Invention

According to the present invention, during a predetermined period prior to detection of the sensor output, a state is induced in which a voltage is not applied between the pair of electrodes or in which a potential difference between the pair of electrodes is less than a reference value. As a result, during the predetermined period, decomposition of NOx on the electrodes can be suppressed and a large amount of NOx can be caused to adsorb on the electrodes. Accordingly, a sensor output detected after the predetermined period elapses can be made a large output. Consequently, NOx concentrations can be detected over a wide range that also includes a case in which a NOx concentration is an extremely low concentration. Further, since the sensor output can be made a large output, the influence of output errors that arise due to noise or the like can be suppressed, and the NOx concentration can be detected with a high degree of accuracy.

Further, hunting of the sensor output that is caused by application of a voltage for sensor output detection can be suppressed by using an alternating voltage as the voltage for sensor output detection or by applying a voltage in the opposite direction to the voltage for sensor output detection after applying the voltage for sensor output detection.

Further, by setting the length of the predetermined period, the maximum value of the voltage for sensor output detection, or the application time period of the voltage for sensor output detection in accordance with the operating state of the internal combustion engine, for example, in a case where the NOx concentration is a low concentration, control can be performed that is in accordance with the operating state, such as lengthening the predetermined period or the application time period or increasing the applied voltage.

Further, by making the length of the predetermined period, the maximum value of the voltage for sensor output detection, or the application time period of the voltage for sensor output detection different values for each of two NOx sensors that are arranged upstream and downstream of a urea SCR system, appropriate control can be performed in accordance with the usage environment of each of the two NOx sensors.

In addition, by applying a voltage for impedance detection after application of a voltage for sensor output detection, the element temperature can be detected in parallel with control for detecting the NOx concentration.

Furthermore, during a period until the sensor element of the NOx sensor reaches an activation temperature, by applying a direct-current voltage between the pair of electrodes or by applying an alternating voltage therebetween at fixed intervals, it is possible to suppress the adherence of a large amount of NOx to the electrodes before the sensor element reaches the activation temperature. Accordingly, control for NOx concentration detection can be executed at an earlier stage after the sensor element reaches the activation temperature.

BRIEF DESCRIPTION OF DRAWINGS

FIG. 7 is a diagram for describing a map that is used in Embodiment 2 of the present invention, in which a relationship between sensor output of NOx sensor and NOx concentration is defined.

DESCRIPTION OF EMBODIMENTS

Figure 1:
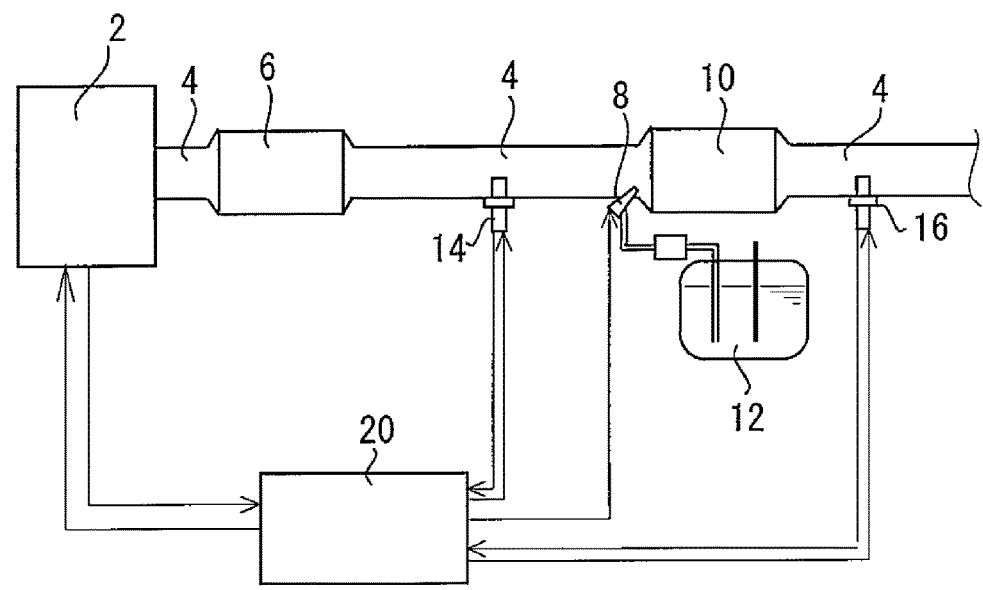
FIG. 1 is a view for describing the overall configuration of a system of Embodiment 1 of the present invention.

Embodiments of the present invention are described hereunder with reference to the accompanying drawings. For each of the drawings, the same or corresponding portions are denoted by the same reference numerals, and a description of such portions is simplified or omitted.

Embodiment 1

Overall Configuration of System of Embodiment 1

FIG. 1 is a view for describing the overall configuration of a system of Embodiment 1 of the present invention. The system illustrated in FIG. 1 is mounted in a vehicle or the like and used. In the system illustrated in FIG. 1, a DPF (diesel particulate filter) 6 that is a filter for trapping particles is arranged in an exhaust passage 4 of an internal combustion engine 2. Although not illustrated in the drawings, an oxidation catalyst is combined with and disposed in the DPF 6. The DPF 6 is a filter that traps particulate matter (PM) that is contained in exhaust gas.

A urea SCR system (hereunder, also referred to as "SCR system") is disposed downstream of the DPF 6 in the exhaust passage 4. The SCR system includes a urea injection valve 8 and a selective reduction NOx catalyst 10. The urea injection valve 8 is connected through piping to a urea tank 12. The urea injection valve 8 injects urea water that is supplied from the urea tank 12 into the exhaust passage 4 on the upstream side of the NOx catalyst 10. The NOx catalyst 10 reduces NOx contained in exhaust gas by utilizing ammonia generated from the urea water as a reducing agent, to thereby purify the exhaust gas.

A NOx sensor 14 (first NOx sensor) is arranged in the exhaust passage 4 at a position that is upstream of the NOx catalyst 10 and downstream of the DPF 6. A NOx sensor 16 (second NOx sensor) is arranged in the exhaust passage 4 on the downstream side of the NOx catalyst 10.

This system includes a control device 20. In addition to the NOx sensor 14 and the NOx sensor 16, an air/fuel ratio sensor and various sensors of the internal combustion engine 2 are connected to the input side of the control device 20. The urea injection valve 8 and various other actuators are connected to the output side of the control device 20. The control device 20 executes a predetermined program based on information inputted from the various sensors to actuate various actuators and the like and thereby execute various kinds of control relating to operation of the internal combustion engine 2.

Configuration of NOx Sensor of Embodiment 1

Figure 2:
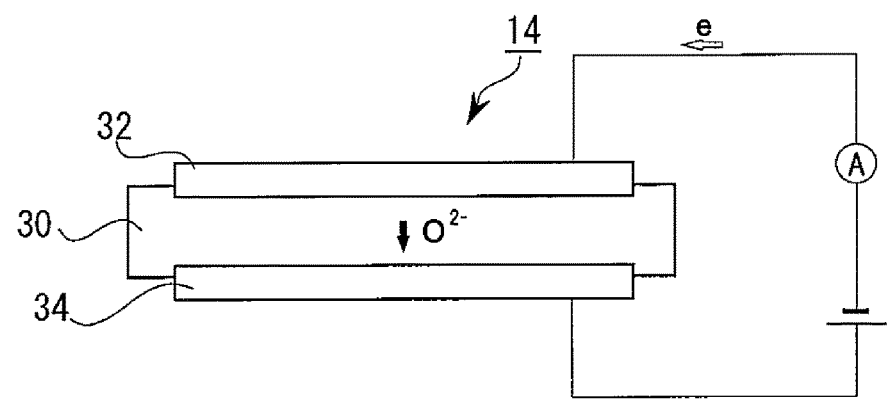
FIG. 2 is a schematic diagram for describing the configuration of a sensor element of the NOx sensor 14 of Embodiment 1 of the present invention.

FIG. 2 is a schematic diagram for describing the configuration of a sensor element of the NOx sensor 14 of the present Embodiment 1. Note that although the NOx sensor 14 is taken as an example in the following description, the NOx sensor 16 on the downstream side of the NOx catalyst 10 has the same configuration as the NOx sensor 14.

The NOx sensor 14 is a single-cell type sensor. More specifically, as shown in FIG. 2, the sensor element of the NOx sensor 14 includes one cell that has a solid electrolyte 30, and a pair of electrodes that include a detection electrode 32 and a reference electrode 34 which are disposed so as to sandwich the solid electrolyte 30 therebetween. The solid electrolyte 30 is composed of zirconia ($ZrO_2$). The detection electrode 32 of the NOx sensor 14 is a perovskite-type electrode. A perovskite-type electrode has selective adsorptivity with respect to NOx. The reference electrode 34 is an electrode that includes platinum (pt).

Note that, an insulating substrate having a predetermined concave portion is disposed on a side of a face on which the reference electrode 34 is disposed of the solid electrolyte 30, and the reference electrode 34 is disposed in a space formed by the concave portion of the insulating substrate and the solid electrolyte 30. A heater is formed inside the insulating substrate.

The configuration is such that a voltage for detecting a NOx concentration is applied through an electric circuit or the like between the detection electrode 32 and the reference electrode 34 that are the pair of electrodes, and a predetermined alternating voltage (AC voltage) for detecting the element temperature is also applied between the detection electrode 32 and the reference electrode 34. Further, a predetermined voltage is applied through an electric circuit or the like to the heater to thereby heat the sensor element.

Control of Embodiment 1

In the present Embodiment 1, control that the control device 20 executes includes control of a voltage applied to the NOx sensors 14 and 16, and control to detect output signals of the NOx sensors 14 and 16 to detect a NOx concentration included in exhaust gas upstream or downstream of the SCR system.

NOx is selectively adsorbed on the surface of the detection electrode 32 that is a perovskite-type electrode. When a predetermined voltage for detecting a sensor output is applied at the time of NOx concentration detection, NOx that has adsorbed on the detection electrode 32 is decomposed and a decomposition current is generated. The NOx sensor 14 outputs a current value at this time. The control device 20 receives the output of the NOx sensor 14 to thereby detect the NOx concentration contained in the exhaust gas.

However, it is considered that the NOx concentration in exhaust gas on the downstream side of the DPF 6 or the downstream side of the NOx catalyst 10 has been purified to an extremely low concentration. Accordingly, a decomposition current generated by NOx decomposition is extremely small. It is considered that, in this case, errors are liable to arise in the output of the NOx sensor 14 and NOx sensor 16 due to the influence of noise or the like, and consequently variations arise in the detected NOx concentrations.

Figure 3:
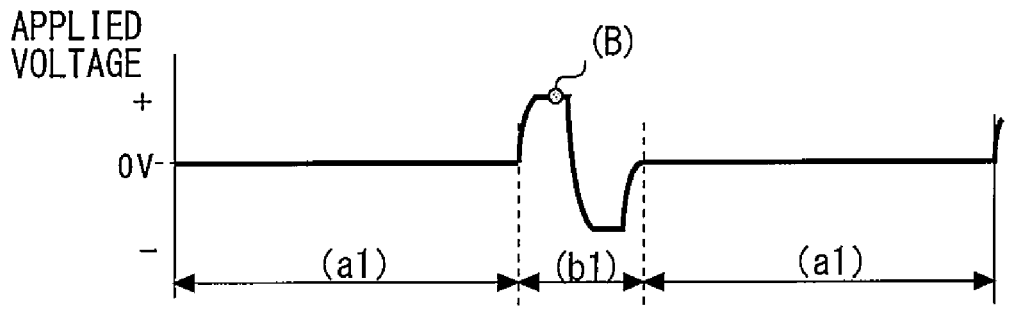
FIG. 3 is a diagram for describing summery of a control of Embodiment 1 of the present invention.

Therefore, according to the system of the present Embodiment 1, NOx concentration detection is performed under the control described hereunder. FIG. 3 is a timing chart for describing control performed according to the present Embodiment 1. The example in FIG. 3 illustrates changes in a voltage applied between the detection electrode 32 and the reference electrode 34 at a time of NOx concentration detection according to the present Embodiment 1.

NOx Adsorption Period

In a NOx adsorption period (predetermined period) denoted by reference characters (a1) in FIG. 3, application of a voltage to electrodes 32 and 34 is stopped (disconnected). A potential difference between the detection electrode 32 and the reference electrode 34 at this time is 0 V. During the NOx adsorption period, NOx on the detection electrode 32 is not subjected to decomposition, and the amount of NOx adsorbed on the detection electrode 32 gradually increases.

NOx Detection Period

In a NOx detection period denoted by reference characters (b1) in FIG. 3, an alternating voltage as a voltage for output detection is applied between the detection electrode 32 and the reference electrode 34. More specifically, the applied voltage gradually rises from the state in which the voltage is 0 V in the forward direction that makes the detection electrode 32 negative and the reference electrode 34 positive, and the applied voltage is maintained for a fixed time period at a stage at which the applied voltage has reached the maximum voltage. The output during this period in which the applied voltage is maintained at the maximum voltage is monitored, and an output at a detection timing (B) at which the maximum output is emitted is detected as the sensor output.

After the applied voltage has been maintained for a fixed time period at the maximum voltage, the voltage is gradually decreased, and gradually falls as far as a minimum voltage that makes the reference electrode 34 negative and the detection electrode 32 positive. Here, the terms "maximum voltage" and "minimum voltage" refer to voltages of the same size in opposite directions centering on 0 V that is the voltage during the NOx adsorption period. The voltage is maintained for a fixed time period at the stage at which the minimum voltage is reached. By applying voltages of the same size for the same time periods on the positive side and the negative side in this manner, the occurrence of hunting can be prevented by a reverse current after application of an alternating voltage, and a "NOx adsorption period" can be quickly returned to.

In the present embodiment, it is assumed that an alternating voltage is applied for only one cycle. Further, in the following embodiments, it is assumed that the term "size of the alternating voltage" means a maximum voltage, a difference between the maximum voltage and the minimum voltage of the alternating voltage is also referred to as an "amplitude", and the reciprocal of a length of one cycle of an applied alternating voltage is also referred to as a "frequency".

In this connection, if the NOx adsorption period is made a long period, a large amount of NOx can be caused to adsorb on the detection electrode 32 during the NOx adsorption period. Accordingly, a larger sensor output can be detected in the NOx detection period. On the other hand, a NOx concentration cannot be detected during the NOx adsorption period. Consequently, a corresponding response delay arises. Therefore, a reference time period as the length of the NOx adsorption period is set to an appropriate value that is determined by experimentation or the like that takes into consideration a time period in which NOx of an amount needed to obtain a sensor output of a required size can be adsorbed as well as the response delay caused by the NOx adsorption period. This value is stored in advance in the control device 20. More specifically, for example, it is preferable that a length of time taken to detect the NOx concentration once from the start of the NOx adsorption period until the end of the NOx detection period is set to a value between approximately 0.1 and 10 seconds.

There is a correlation between the detected sensor output and the NOx concentration. However, this correlation varies depending on the length of the NOx adsorption period and the size of the alternating voltage applied in the NOx detection period. Accordingly, the relation between the sensor output and the NOx concentration is determined by experimentation or the like in consideration of the sensor characteristics and the length of the NOx adsorption period, as well as the size and cycle of the alternating voltage applied in the NOx detection period. As a result, a map defining the relation between the sensor output and the NOx concentration is obtained, and the map is stored in advance in the control device 20. In the actual control, the NOx concentration is determined in accordance with the map according to the detected sensor output.

Specific Control of Embodiment 1

Figure 4:
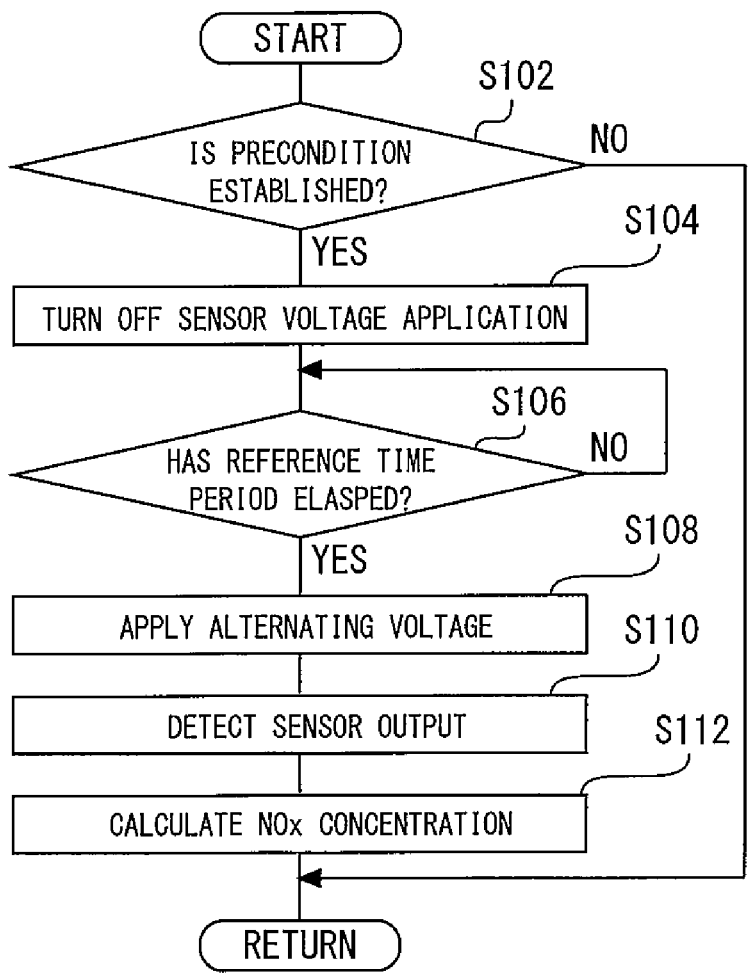
FIG. 4 is a flowchart for describing a routine of control that is executed by the control device 20 in Embodiment 1 of the present invention.

FIG. 4 is a flowchart for describing a routine of control that the control device 20 executes in Embodiment 1 of the present invention. The routine in FIG. 4 is repeatedly executed at a fixed operation cycle. Note that the NOx sensor 14 on the upstream side is described as the object of control in the present embodiment.

In the routine shown in FIG. 4, first, control device 20 determines whether or not a precondition is established (S102). The precondition is a necessary condition for appropriately detecting NOx by means of the NOx sensor 14 and, for example, is a condition regarding whether the vehicle is operating after warming-up of the internal combustion engine 2, or whether the sensor element of the NOx sensor 14 has reached an activation temperature or the like. It is assumed that a specific precondition is set beforehand and stored in the control device 20. If it is determined in step S102 that the precondition is not established, the current processing ends temporarily.

If it is determined in step S102 that the precondition is established, the control device 20 then turns off the application of a voltage to the electrodes 32 and 34 (S104). As a result, the potential difference between the electrodes 32 and 34 becomes approximately 0 V, and the above described NOx adsorption period begins.

Next, the control device 20 determines whether or not a reference time period has elapsed since application of the voltage was turned off (S106). That is, the control device 20 determines whether or not the NOx adsorption period has ended. Here, if the control device 20 determines that the reference time period has not elapsed, in a state in which application of a voltage is turned off, the determination processing in step S106 is repeatedly executed until it is determined that the reference time period has elapsed.

On the other hand, when it is determined in step S106 that the reference time period has elapsed, the control device 20 applies an alternating voltage as a NOx detection voltage (S108). In this case, as shown in FIG. 3, as the alternating voltage, a voltage is applied so as to gradually rise towards the maximum voltage in the forward direction. Thereafter, the voltage is maintained at the maximum voltage and thereafter the voltage is gradually lowered towards the minimum voltage. Thereafter, the voltage is maintained at the minimum voltage, and is then gradually returned to 0 V.

The sensor output is monitored during the period in which the voltage in the forward direction is being applied after the start of application of the alternating voltage in step S108, and an output that is the maximum value is detected as the sensor output (S110). Next, a NOx concentration is calculated based on the sensor output (S112). The NOx concentration is calculated according to the sensor output in accordance with a map or the like that defines the relationship between the sensor output and the NOx concentration. Thereafter, the current processing ends.

Advantageous Effects of Embodiment 1

Figure 5:
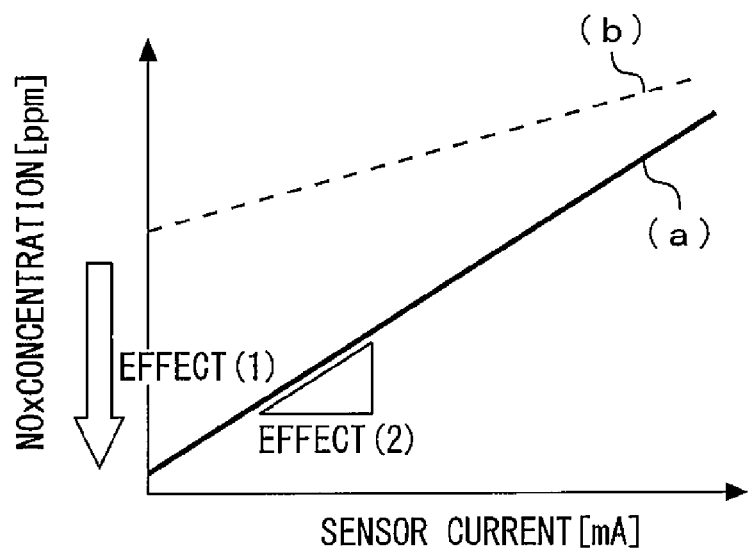
FIG. 5 is a diagram for describing an accuracy of the NOx concentration detection of embodiment of the present invention.

FIG. 5 is a view for describing the relation between the sensor output and NOx concentration in Embodiment 1 of the present invention. In FIG. 5, the horizontal axis represents the sensor output (current) and the vertical axis represents the NOx concentration. Further, in FIG. 5, a solid line (a) represents detection values in the present Embodiment 1, and a broken line (b) represents detection values according to the conventional detection method.

As shown in FIG. 5, the following two advantageous effects can be obtained by the control of the present Embodiment 1.

Advantageous Effect 1

According to the conventional detection method, in a region of an extremely low concentration, there is a concentration region in which an adequate sensor output cannot be obtained and a concentration cannot be detected by the NOx sensor 14. However, according to the present Embodiment 1, by detecting a decomposition current after adsorption of NOx has been adequately performed, a NOx concentration can also be detected with respect to the extremely low concentration region. Thus, it is possible to ensure that a wide range of NOx concentrations can be detected by the NOx sensor 14.

Advantageous Effect 2

According to the present Embodiment 1, a decomposition current is detected as a sensor output after NOx has been caused to adsorb on electrodes. Accordingly, the amount of the decomposition current that is detected can be increased. That is, as shown in FIG. 5, in comparison to the conventional case (b), the rate of change in the sensor current (output) with respect to a change in the NOx concentration can be increased. Therefore, the output of the NOx sensor 14 is not liable to be affected by noise or the like, and it is difficult for variations to arise in the output. Therefore, according to the system of the present Embodiment 1, a NOx concentration can be detected with a high degree of accuracy by the NOx sensor 14. Further, since the sensor output value can be made a large value, for example, it is no longer necessary to provide an amplifier or the like between the control device 20 and the NOx sensor 14. Therefore, the cost of the overall system that includes the NOx sensor 14 can be reduced.

Note that, according to the present Embodiment 1, because the applied voltage is stopped during the NOx adsorption period in order to cause NOx to adsorb, a delay arises in the sensor output. However, even if the reference time period for which the NOx adsorption period is maintained is an extremely short time period, the sensor output obtained based on the NOx adsorption can be increased to a certain extent. Thus, compatibility can be achieved between ensuring the necessary output responsiveness of the NOx sensor and improving the accuracy of the NOx concentration detection.

Other Example of Embodiment 1

According to the present Embodiment 1, a case has been described in which application of the voltage is turned off during the NOx adsorption period. However, the present invention is not limited thereto, and a configuration may also be adopted that applies a voltage so that a potential difference between the detection electrode 32 and the reference electrode 34 becomes 0 V or a value equal to or less than a reference value that is set in the vicinity of 0 V. Here, it is assumed that the reference value is a value that is at least less than a maximum voltage of the alternating voltage applied during the NOx detection period. Further, the reference value is set in a small range in which decomposition of NOx at the detection electrode is not promoted. This similarly applies with respect to the embodiments described hereinafter.

Further, according to the present Embodiment 1, a case in which an alternating voltage is applied during the NOx detection period has been described. This is done to suppress the occurrence of hunting with respect to the sensor output after application of the alternating voltage, by applying a voltage of the same size in the opposite direction so as to be symmetrical with the voltage applied in the forward direction. However, in the present invention, application of a voltage for NOx detection is not necessarily limited to application of an alternating voltage. In the present invention, for example, a configuration may be adopted in which a single-pulse voltage of a predetermined size is applied as a voltage for output detection in a direction that decomposes NOx that is present on the detection electrode 32. In this case, it is sufficient to start the NOx adsorption period again after the hunting has converged. This similarly applies with respect to the embodiments described hereinafter.

It is also effective in terms of suppressing hunting to, after applying a single-pulse voltage in this manner, apply a voltage in the opposite direction with respect to which an absolute value is smaller than the maximum value of the voltage for output detection. In such a case, it is preferable to set a value obtained by integrating the applied voltage in the forward direction over the application time period (area of the waveform on the positive side of the alternating voltage in FIG. 3) and a value obtained by integrating the applied voltage in the opposite direction over the application time period (area of the waveform on the negative side of the alternating voltage in FIG. 3) so as to be the same. That is, in a case where the absolute value of the applied voltage in the opposite direction is made small, it is desirable to lengthen the application time period of the voltage in the opposite direction. This similarly applies with respect to the embodiments described hereinafter.

In addition, according to the present embodiment, a case has been described in which the sensor output during application of an alternating voltage in the forward direction in the NOx detection period is monitored, and the maximum output at such time is used as the sensor output. However, the present invention is not limited thereto, and for example, a configuration may be adopted in which an average value of the sensor output during application of the alternating voltage in the forward direction is determined, and the average value is adopted as the sensor output. Further, a configuration may be adopted in which the sensor output is detected in a manner that takes a predetermined timing in a period in which a maximum voltage is being applied in the forward direction during the NOx detection period as the timing of the output detection. This similarly applies with respect to the embodiments described hereinafter.

In the present Embodiment 1, control of the NOx sensor 14 that is disposed on the upstream side has been described. However, the present invention is not limited thereto, and can also be applied to control of the NOx sensor 16 that is disposed on the downstream side. This similarly applies with respect to the embodiments described hereinafter.

Further, the configuration and the like of the sensor element of the NOx sensor 14 described in the present Embodiment 1 are not intended to restrict the present invention. For example, although the present Embodiment 1 describes a case in which a perovskite-type electrode is used as the detection electrode 32, the present invention is not limited thereto, and another kind of electrode having a NOx adsorption property may also be used. Further, the solid electrolyte 30 and the reference electrode 34 are not limited to those described in the present Embodiment 1. This similarly applies with respect to the embodiments described hereinafter. Furthermore, a sensor configuration that does not have an insulating substrate or a heater on the reference electrode 34 side may also be adopted. This similarly applies with respect to the embodiments described hereinafter.

Likewise, the system of Embodiment 1 of the present invention is not limited to the system shown in FIG. 1. That is, in the NOx sensor control device of the present invention, the NOx sensors are not limited to sensors that are arranged on the upstream and downstream sides of the urea SCR system, and may be sensors that are arranged at other positions. This similarly applies with respect to the embodiments described hereinafter.

Embodiment 2

The configuration of the system and configuration of the NOx sensors of the present Embodiment 2 are the same as the respective configurations of the system and NOx sensors illustrated in FIGS. 1 and 2. The system of the present Embodiment 2 controls the two sensors, namely, the NOx sensor 14 on the upstream side and the NOx sensor 16 on the downstream side. Although the method for controlling the NOx sensor 14 and the NOx sensor 16, respectively, is the same as in Embodiment 1, the length of the NOx adsorption period and the amplitude and cycle of the alternating voltage that is applied in the NOx detection period differ between the two NOx sensors 14 and 16, and furthermore, a map defining a relation between the sensor output and the NOx concentration that is used when calculating a NOx concentration differs between the two NOx sensors 14 and 16.

Figure 6:
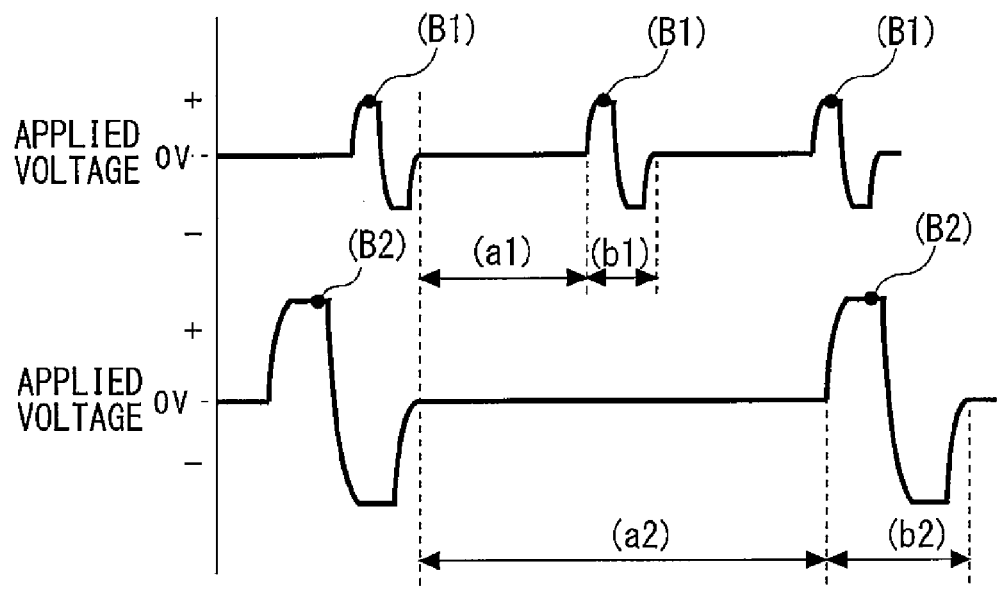
FIG. 6 is a diagram for describing summery of a control of Embodiment 2 of the present invention.

FIG. 6 is a timing chart for describing control in Embodiment 2 of the present invention. In FIG. 6, a waveform on the upper side represents a voltage applied to the NOx sensor 14 on the upstream side, and a waveform on the lower side represents a voltage applied to the NOx sensor 16.

As described above, in the NOx catalyst 10, NOx contained in exhaust gas is purified by ammonia. Accordingly, the NOx concentration of the exhaust gas that is a detection object of the NOx sensor 16 on the downstream side of the NOx catalyst 10 is an extremely low concentration relative to the NOx concentration of the exhaust gas that is a detection object of the NOx sensor 14 on the upstream side of the NOx catalyst 10.

Accordingly, the reference time periods which are the lengths of the respective NOx adsorption periods (a1 and a2) are set so that the reference time period for the NOx sensor 16 on the downstream side is longer than the reference time period for the NOx sensor 14 on the upstream side. In addition, the maximum voltage of an alternating voltage applied in the NOx detection periods (b1 and b2) is set so that the maximum voltage applied with respect to the NOx sensor 16 on the downstream side is larger than the maximum voltage applied with respect to the NOx sensor 14 on the upstream side. Further, the cycle of the alternating voltage is set so that the cycle of the alternating voltage applied with respect to the NOx sensor 16 on the downstream side is longer than the cycle of the alternating voltage applied with respect to the NOx sensor 14 on the upstream side.

Similarly to Embodiment 1, among the outputs monitored during application of the maximum voltage in the NOx detection periods (b1 and b2), the maximum outputs (for example, outputs at B1 and B2) are detected as sensor outputs of the respective NOx sensors 14 and 16.

In a case where the reference time periods, or the size or time period of the alternating voltages are different, the correlation between the sensor output (current value) and the NOx concentration will differ in accordance therewith. For example, a NOx adsorption amount with respect to the same NOx concentration will increase if the NOx adsorption period is lengthened. Accordingly, the longer that the NOx adsorption period is, the larger the sensor output that will be obtained. That is, when sensor outputs that are the same are compared, the longer that the NOx adsorption time period was, the smaller that the actual NOx concentration is. Likewise, with respect to gases which contain the same NOx concentrations, a larger sensor current will flow with respect to the gas for which the alternating voltage for output detection is larger or for which the application time period of the alternating voltage is longer.

Accordingly, as shown in FIG. 7, according to the present Embodiment 2, maps are prepared that define different relations between the sensor output (current value) and NOx concentration for each of the NOx sensors 14 and 16 on the upstream side and downstream side. NOx concentrations in accordance with outputs are calculated according to the map on the upper side in FIG. 7 for the NOx sensor 14 on the upstream side, and NOx concentrations in accordance with outputs are calculated in accordance with the map on the lower side in FIG. 7 for the NOx sensor 16 on the downstream side. Comparing the two maps shown in FIG. 7, it is found that the NOx concentrations calculated with respect to the same outputs are larger for the NOx sensor 14 on the upstream side than for the NOx sensor 16 on the downstream side.

Note that maps of this kind differ depending on the length of the reference time period or the maximum voltage and cycle of the alternating voltage for the NOx sensors 14 and 16, respectively, or depending on the respective characteristics of the NOx sensors 14 and 16 and the like, and the appropriate relations are determined by experimentation or the like and stored in the control device 20.

As described above, in the present Embodiment 2, the length of the reference time period, the maximum voltage of the alternating voltage during the NOx detection period, and the application time period are each set to correspond to differences in the NOx concentrations that are due to the difference between the installation positions of the NOx sensors 14 and 16. It is thereby possible to perform appropriate control in accordance with the respective environments in which NOx concentrations are different, and improve the accuracy of detecting the NOx concentrations.

According to the present Embodiment 2, a case has been described in which the NOx sensors 14 and 16 installed on the upstream side and downstream side of the NOx catalyst 10 of the urea SCR system, respectively, are controlled. However, the installation positions of the NOx sensors in the present invention are not limited to the aforementioned positions. The control of the present Embodiment 2 can be applied to a case of controlling two or more NOx sensors that are used in an environment in which the NOx concentrations of exhaust gas that is the detection object are predicted to differ. This similarly applies in a case where the present Embodiment 2 is applied to the following embodiments.

Further, according to the present Embodiment 2 a case has been described in which it is assumed that the length of the NOx adsorption period as well as the maximum voltage and the application time period of the alternating voltage all differ between the NOx sensor 14 and the NOx sensor 16. However, the present invention is not limited thereto, and it is sufficient to assume that one or more factors among the length of the NOx adsorption period, the maximum voltage of the alternating voltage, and the application time period (cycle) of the alternating voltage differ in accordance with a difference between the environments in which the NOx sensors are installed. This similarly applies in a case where the present Embodiment 2 is applied to the following embodiments.

In addition, according to the present Embodiment 2 a case has been described in which a map that defines the relation between the NOx concentration and the output is provided for each of the NOx sensor 14 and the NOx sensor 16, and NOx concentrations are detected based on the respective maps. However, the present invention is not limited thereto, and for example, a configuration may also be adopted in which a correction coefficient is calculated in accordance with a control target value (the length of a NOx adsorption period, the maximum voltage or the application time period of the alternating voltage or the like) of the applied voltage, and the sensor output or NOx concentration is corrected based on the correction coefficient. This similarly applies in a case where the present Embodiment 2 is applied to another embodiment.

Embodiment 3

The configurations of the system and NOx sensors of Embodiment 3 are identical to the configurations of the system and NOx sensors illustrated in FIG. 1 and FIG. 2. According to Embodiment 2 of the present invention, a case has been described in which the length of the NOx adsorption period and the size and the cycle of the alternating voltage and the like are set in advance for the NOx sensors 14 and 16 on the upstream and downstream sides, respectively. In contrast, in the system of Embodiment 3, a reference time period (length of NOx adsorption period), and a maximum voltage and a cycle (application time period) of the alternating voltage are set during control that is performed with respect to the single NOx sensor 14.

According to the present Embodiment 3, the length of a NOx adsorption period, the maximum voltage of the alternating voltage or the length of a cycle thereof are set in accordance with differences in NOx concentrations that are predicted based on the operating state. For example, the NOx concentration is liable to increase when cold-starting the internal combustion engine 2 or during high-load operation thereof. In an environment in which the NOx concentration increases in this manner, the NOx adsorption time period is shortened, the maximum voltage of the alternating voltage is reduced, and the cycle of the alternating voltage is shortened. Even when this configuration is adopted, it is possible to obtain a sensor output that is large to a certain extent with respect to the NOx concentration. Further, by shortening the NOx adsorption time period, the responsiveness of the NOx sensor 14 can be speeded up to correspond to a time of high-load operation at which fast responsiveness is required.

On the other hand, the overall NOx concentration is liable to be low while the internal combustion engine 2 is stopped during idle-stop control or during a fuel-cut operation of the internal combustion engine 2. Under such operating conditions in which the NOx concentration is predicted to be low, the NOx adsorption period is lengthened, the maximum voltage of the alternating voltage is increased, and the cycle thereof is shortened. It is thereby possible to ensure a sensor output of a certain extent with respect to even an extremely low NOx concentration.

According to the present Embodiment 3, a plurality of categories are set based on a plurality of conditions such as the temperature at startup, the current load, whether or not a fuel-cut operation is being performed, and whether or not the internal combustion engine is currently stopped for idle-stop control, and combinations of control target values of the applied voltage that include the length of a NOx adsorption period (reference time period) and the maximum voltage and the cycle of the alternating voltage are set as maps for each category and stored in advance in the control device 20. At the time of actual control, the current operating states are detected based on the outputs of various sensors and the like, and applied voltage control target values are set with respect to the NOx sensor 14 based on the map of applied voltages corresponding thereto.

Figure 8:
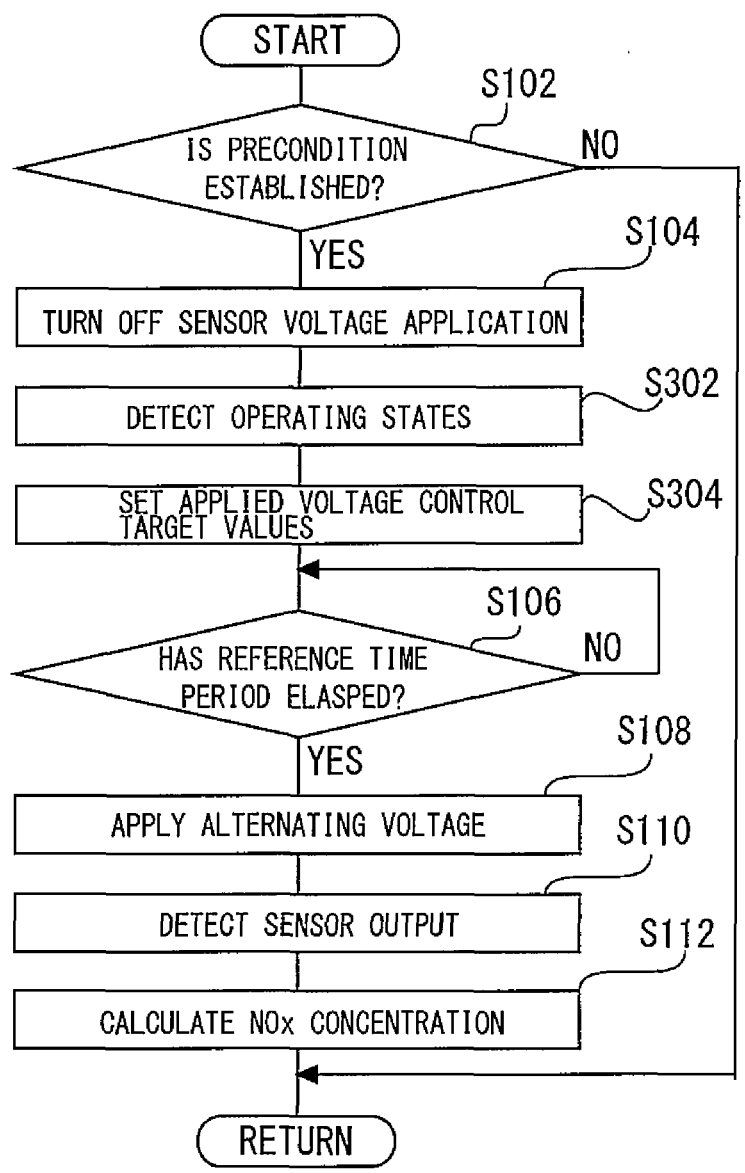
FIG. 8 is a flowchart for describing a routine of control that is executed by the control device in Embodiment 3 of the present invention.

FIG. 8 is a view for describing a routine of control that the control device executes in Embodiment 3 of the present invention. The routine illustrated in FIG. 8 is identical to the routine illustrated in FIG. 4 except that FIG. 8 includes the processing in steps S302 to S304 between the processing in step S104 and the processing in step S106.

More specifically, when it is determined that the precondition is established, and application of a voltage is turned off (S104), various operating states are then detected (302). The current operating states of the internal combustion engine 2 are detected in accordance with the outputs of various sensors and the like.

Next, control target values of the applied voltage are set in accordance with the detected operating states (S304). More specifically, in this case, the reference time period that is the length of the NOx adsorption period, and the maximum voltage and the cycle of the alternating voltage to be applied in the NOx detection period are set, respectively. These control target values are set according to the detected operating states in accordance with the maps stored in the control device 20.

Thereafter, it is determined whether or not the reference time period has elapsed (S106). Here, it is determined whether or not the reference time period set in step S304 has elapsed since the applied voltage was turned off in step S104. If the result determined in step S106 is negative, the determination in step S106 is repeated until it is determined that the reference time period has elapsed.

On the other hand, if the result determined in step S106 is that the reference time period has elapsed, next, an alternating voltage is applied. The maximum voltage and the cycle of the alternating voltage are controlled to the values set in step S304. The maximum output during this application of the alternating voltage is detected as the sensor output (S110).

Next, the NOx concentration is determined in accordance with the detected sensor output (S112). Here, the NOx concentration corresponding to the sensor output is determined according to a map in accordance with voltage application conditions set in step S304. Thereafter, the current processing ends.

As described above, according to the present Embodiment 3, in a case where the NOx concentration differs depending on the operating state, it is possible to appropriately control the applied voltage in accordance with such a difference. More specifically, for example, the overall detection time period is shortened under an environment in which the load is high and faster detection of the NOx concentration is demanded. Further, in a case where the NOx concentration is a low concentration, the NOx adsorption period can be set to a longer period and a larger output can be detected. It is thereby possible to detect the NOx concentration with a higher degree of accuracy.

According to the present Embodiment 3 a case has been described in which a plurality of operating states are detected, and the reference time period, and the maximum voltage and the cycle of the alternating voltage are respectively set in accordance with the plurality of operating states. However, the present invention is not limited thereto. For example, a configuration may be adopted in which the reference time period, the maximum voltage of the voltage for output detection or the amplitude of the alternating voltage, and the cycle of the alternating voltage or the like are changed. This similarly applies for a case where the control of the present Embodiment 3 is applied to another embodiment.

Further, according to the present Embodiment 3 a case has been described in which control target values of the applied voltage for the single NOx sensor 14 are set in accordance with operating states. However, the present invention is not limited thereto, and a configuration may also be adopted in which, when controlling a plurality of NOx sensors, control target values of the applied voltage are set according to the operating states for the respective NOx sensors, as in Embodiment 2. This similarly applies for a case where the control of the present Embodiment 3 is applied to another embodiment.

Furthermore, according to the present Embodiment 3, a case has been described in which a map is provided that defines the relation between the NOx concentration and the output in accordance with the control target values that are set, and the NOx concentration is detected based thereon. However, the present invention is not limited thereto. For example, a configuration may also be adopted in which a correction coefficient is calculated in accordance with a control target value of the applied voltage, and the sensor output or the NOx concentration is corrected based on the correction coefficient. This similarly applies for a case where the present embodiment is applied to another embodiment.

Embodiment 4

The configurations of the system and NOx sensors of the present Embodiment 4 are identical to the configurations in FIG. 1 and FIG. 2. According to the present Embodiment 4, similarly to Embodiment 1, when detecting the NOx concentration, in addition to control that establishes a NOx adsorption period and an alternating voltage application period, control for detecting the element temperature of the NOx sensor 14 is executed.

An impedance of the solid electrolyte 30 that is detected when a high-frequency alternating voltage is applied between the electrodes 32 and 34 has a high correlation with the sensor element temperature. Accordingly, the element temperature can be detected by detecting the impedance. According to the present Embodiment 4, in addition to the control of Embodiment 1, control is executed that detects the element temperature of the NOx sensor 14 based on the impedance.

Figure 9:
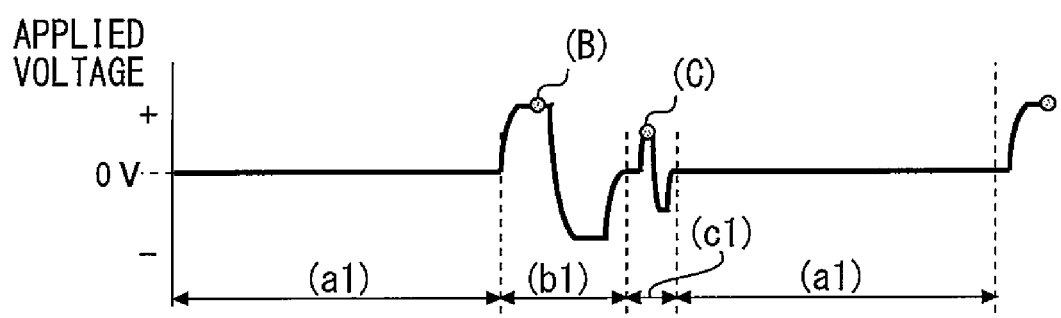
FIG. 9 is a diagram for describing summery of a control of Embodiment 4 of the present invention.

FIG. 9 is a timing chart for describing the control of Embodiment 4 of the present invention. As shown in FIG. 9, according to the present Embodiment 4, similarly to Embodiment 1, a NOx adsorption period (a1) is established to cause NOx to adsorb on the electrodes. After a sufficient amount of NOx is adsorbed, the NOx detection period (b1) is entered. In the NOx detection period (b1), an alternating voltage is applied as a voltage for output detection. At such time, the sensor output is monitored and, for example, the maximum output at a timing (B) in FIG. 9 is detected as the sensor output.

Thereafter, an element temperature detection period (c1) is established. In the element temperature detection period (c1), an alternating voltage is applied as a voltage for detecting the impedance of the solid electrolyte 30. It is assumed that the alternating voltage for impedance detection has, at least, a higher frequency (shorter cycle) and a smaller amplitude relative to the frequency and amplitude of the alternating voltage applied in the NOx detection period. More specifically, for example, the frequency of the alternating voltage for output detection is set to between 0.1 Hz and 10 Hz, and the alternating voltage for impedance detection is set to a frequency of approximately 1 kHz or more, and the maximum voltage value thereof is approximately 0.1 V or less. After the end of the element temperature detection period (c1), the control returns to the NOx adsorption period (a1).

Thus, according to the present Embodiment 4, during a period of detecting the NOx concentration, the NOx adsorption period (a1), the NOx detection period (b1), and the element temperature detection period (c1) are repeatedly executed in this order.

It is assumed that the alternating voltage applied in the element temperature detection period is a high-frequency voltage and is much smaller than the alternating voltage applied in the NOx detection period. It is thereby possible to suppress decomposition of NOx by the alternating voltage in the element temperature detection period, and a long time period in which NOx is actually adsorbed can be secured without lowering the responsiveness of the NOx sensor 14.

Figure 10:
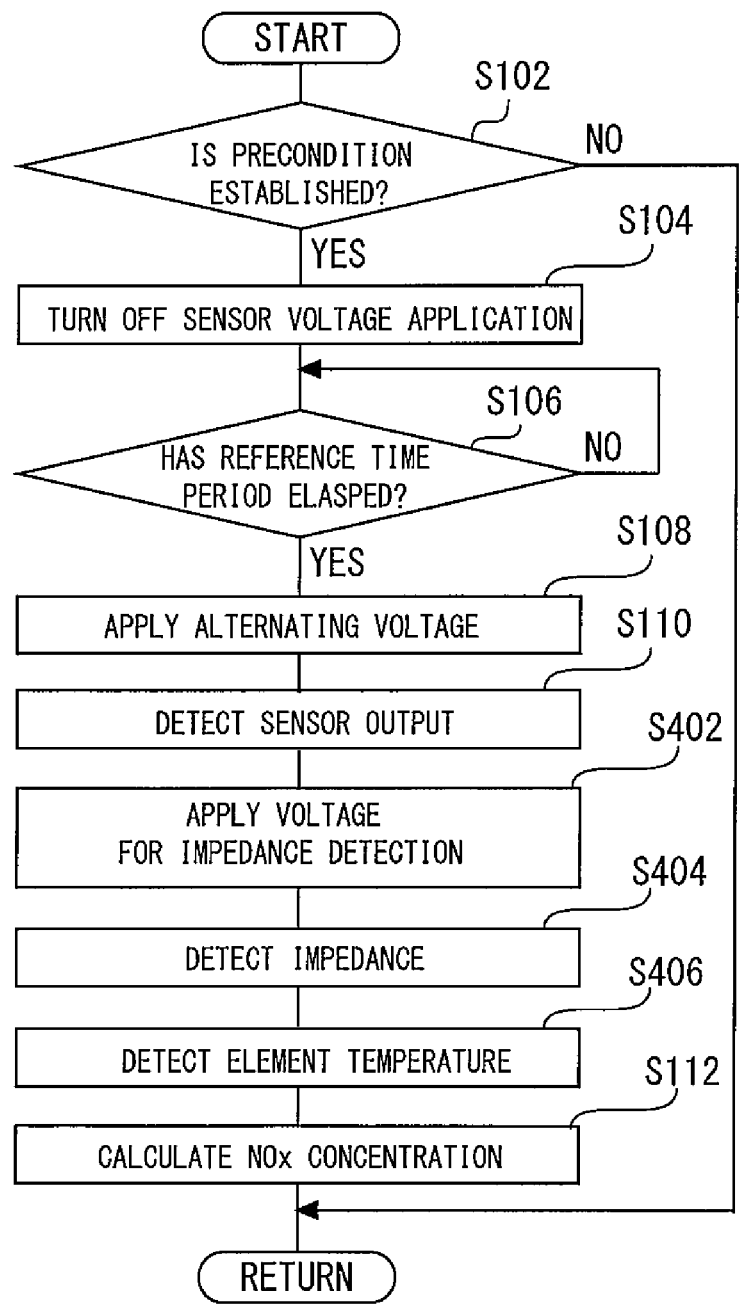
FIG. 10 is a flowchart for describing a routine of control that is executed by the control device in Embodiment 4 of the present invention.

FIG. 10 is a flowchart for describing a routine of control that the control device 20 executes in Embodiment 4 of the present invention. The routine illustrated in FIG. 10 is repeatedly executed at a fixed cycle instead of the routine shown in FIG. 4. The routine shown in FIG. 10 is identical to the routine shown in FIG. 4 except that the routine shown in FIG. 10 includes the processing in steps S402 to S406 between the processing in step S110 and the processing in step S112 of the routine shown in FIG. 4.

In the routine shown in FIG. 10, similarly to the routine shown in FIG. 4, an alternating voltage for output detection is applied during an output detection period (S108), and a maximum output during that period is detected as the sensor output (S110).

Next, an alternating voltage for impedance detection is applied (S402). As described above, in comparison to the alternating voltage for output detection, the alternating voltage for impedance detection is a higher frequency, the application time period thereof is shorter, and the amplitude thereof is smaller. A specific application time period, frequency, and amplitude of the alternating voltage are previously stored in the control device 20.

Next, the impedance is detected at a predetermined detection timing (C) during application of the alternating voltage for impedance detection (S404).

Next, the element temperature is detected (S406). The element temperature is detected according to a map that defines the relation between the impedance and element temperature in accordance with the impedance detected in step S404.

Thereafter, the NOx concentration is detected in accordance with the sensor output detected in step S110 (S112). The NOx concentration is determined according to the element temperature and sensor output in accordance with a map that defines the relation between the element temperature, the sensor output, and the NOx concentration. Thereafter, the current processing ends.

As described above, according to the present Embodiment 4, the element temperature can be detected while suppressing the influence on the NOx concentration detection. The detected temperature can be utilized to detect the NOx concentration, and thus the NOx concentration can be determined with a higher accuracy.

Note that, according to Embodiment 4 a case has been described in which control for detecting the element temperature is combined with the control of Embodiment 1. However, the present invention is not limited thereto, and a configuration may also be adopted in which the control for detecting the element temperature is combined with the control of Embodiment 2 or 3. This similarly applies with respect to the following Embodiment 5.

Embodiment 5

The system and NOx sensors of Embodiment 5 have the same configurations as the system and NOx sensors shown in FIG. 1 and FIG. 2. According to the control of the present Embodiment 5, in addition to the control of Embodiment 4, control is performed that prevents NOx adsorption on the detection electrode 32 before the sensor is activated when starting the internal combustion engine 2.

Figure 11:
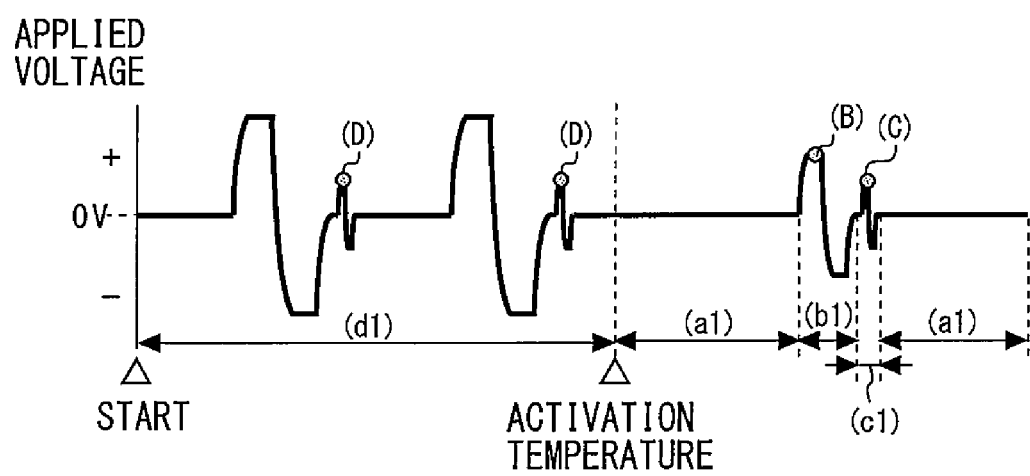
FIG. 11 is a diagram for describing summery of a control of Embodiment 5 of the present invention.

FIG. 11 is a timing chart for describing the control of Embodiment 5 of the present invention. As shown in FIG. 11, according to the present Embodiment 5, after starting the internal combustion engine 2, an alternating voltage is applied at a fixed cycle during a pre-activation period (d1) until the element temperature reaches the activation temperature of the sensor element temperature. The applied alternating voltage is set so that the maximum applied voltage is increased and the cycle (application time period) thereof is lengthened so as to enable adequate decomposition of adsorbed NOx within a range that does not affect the characteristics of the element. Preferably, a voltage is applied with respect to which both the amplitude and cycle are large in comparison to the alternating voltage for NOx detection.

Further, the alternating voltage for impedance detection is applied immediately after applying the alternating voltage for NOx removal in the pre-activation period (d1). Here, at a detection timing (D), the impedance of the solid electrolyte 30 is detected and the element temperature is determined in accordance therewith. The control device 20 determines whether or not the sensor element has reached a predetermined activation temperature based on the element temperature. It is assumed that the alternating voltage for impedance detection that is applied in this case is the same as the alternating voltage for impedance detection that is applied in the element temperature detection period (c1) described in Embodiment 4.

According to the present Embodiment 5, application of an alternating voltage for NOx removal and subsequent application of an alternating voltage for impedance detection are repeated at a fixed cycle during a period until the sensor element reaches an activation temperature. Therefore, NOx that adsorbs on the detection electrode 32 can be removed at a fixed cycle during the pre-activation period, and a state can be induced such that detection of the NOx concentration by the NOx sensor 14 can be started immediately after activation.

Figure 12:
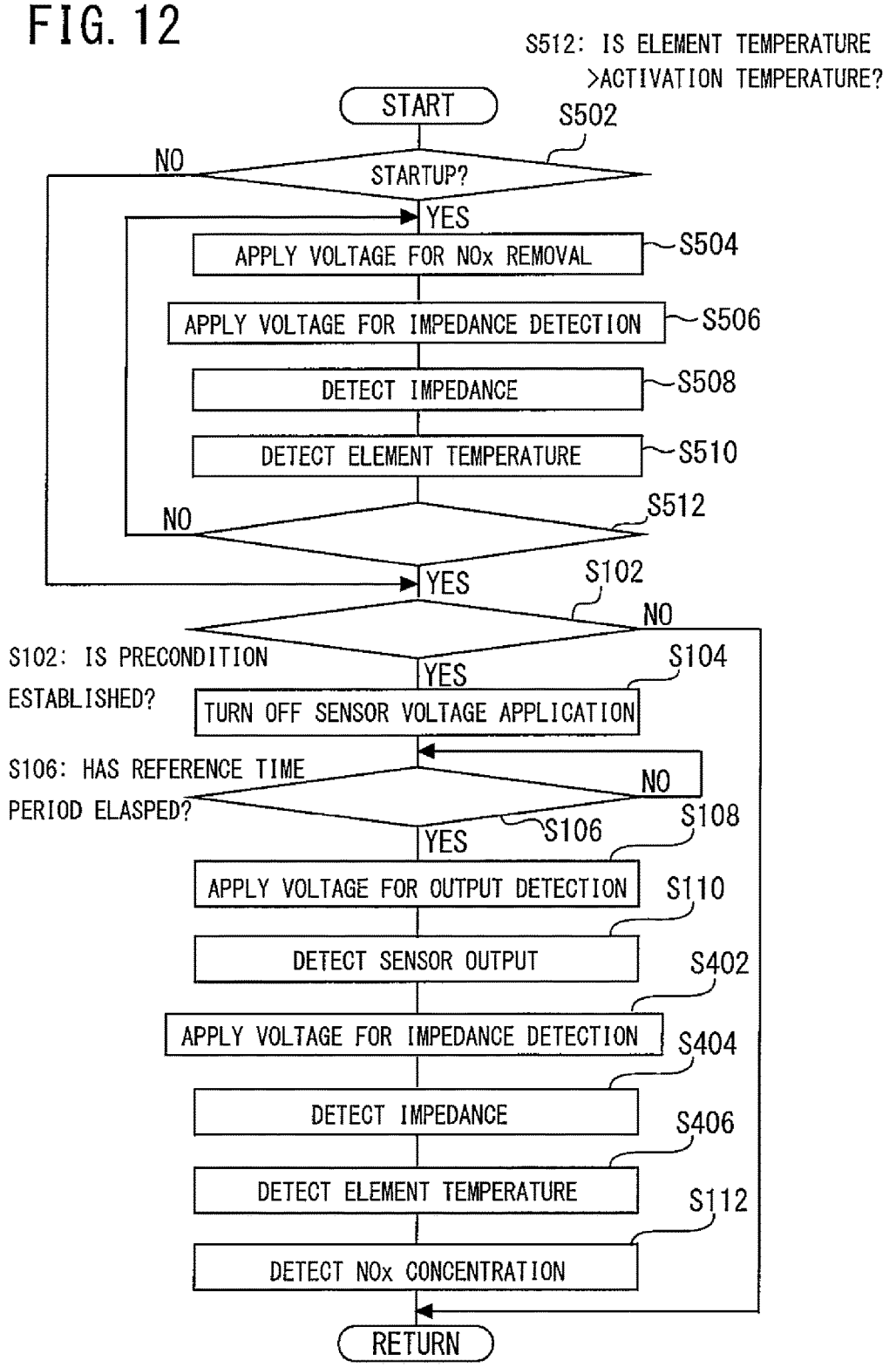
FIG. 12 is a flowchart for describing a routine of control that is executed by the control device in Embodiment 5 of the present invention.

FIG. 12 is a flowchart for describing a routine of control that the control device 20 executes in Embodiment 5 of the present invention. The routine shown in FIG. 12 is executed instead of the routine shown in FIG. 10. The routine shown in FIG. 12 is the same as the routine in FIG. 10 except that the routine in FIG. 12 includes processing in steps S502 to S512 prior to step S102 in the routine shown in FIG. 10.

According to the routine shown in FIG. 12, first, the control device 20 determines whether or not the current state is a state at a time of starting the internal combustion engine 2 (S502). That is, the control device 20 determines whether or not the current processing is initial processing after starting the internal combustion engine 2. If starting of the internal combustion engine 2 is not detected, the control device 20 moves to step S102 to execute the processing in steps S102 to S112 as described above.

On the other hand, if starting of the internal combustion engine 2 is detected, next, an alternating voltage for NOx removal is applied (S504). The amplitude and application time period (cycle) and the like of the alternating voltage for NOx removal to be applied are previously stored in the control device 20.

When the alternating voltage for NOx removal ends, next, the alternating voltage for impedance detection is applied (S506). The amplitude and cycle of the alternating voltage for impedance detection are extremely small in comparison to the alternating voltage for NOx removal and the alternating voltage in the NOx detection period, and specific values of the amplitude and the cycle are previously set and stored in the control device 20.

The impedance is detected at a timing during application of the alternating voltage for impedance detection (S508), and the element temperature is calculated in accordance with the detected impedance (S510). The element temperature is determined based on the detected impedance in accordance with a relation between the impedance and the element temperature that is stored in the control device 20.

Next, the control device 20 determines whether or not the calculated element temperature is higher than the activation temperature (S512). If the control device 20 determines that the element temperature is not higher than the activation temperature, the control device 20 returns to step S504 again. That is, the processing in step S504 to S512 is repeatedly executed at a fixed cycle during a period until the control device 20 determines that the element temperature is greater than the activation temperature in step S512.

On the other hand, if the control device 20 determines that the element temperature is higher than the activation temperature in step S512, the process then transitions to step S102 to execute the processing in steps S102 to S112 in FIG. 10 in a similar manner to Embodiment 4.

As described in the foregoing, according to the present Embodiment 5, a large alternating voltage is applied at a fixed cycle during a period until the sensor element reaches the activation temperature. It is thereby possible to remove NOx that has deposited on the detection electrode 32 at a fixed cycle until the sensor element reaches the activation temperature. Accordingly, detection of the NOx concentration by the NOx sensor 14 can be started at an early stage after the sensor element reaches the activation temperature.

According to the present Embodiment 5 a case has been described in which the control of a pre-activation period of the present Embodiment 5 is added to the control of Embodiment 4. However, the present invention is not limited thereto. For example, a configuration may also be adopted in which the control of the pre-activation period described in Embodiment 5 is added to the control of any of Embodiments 1 to 3.

Figure 13:
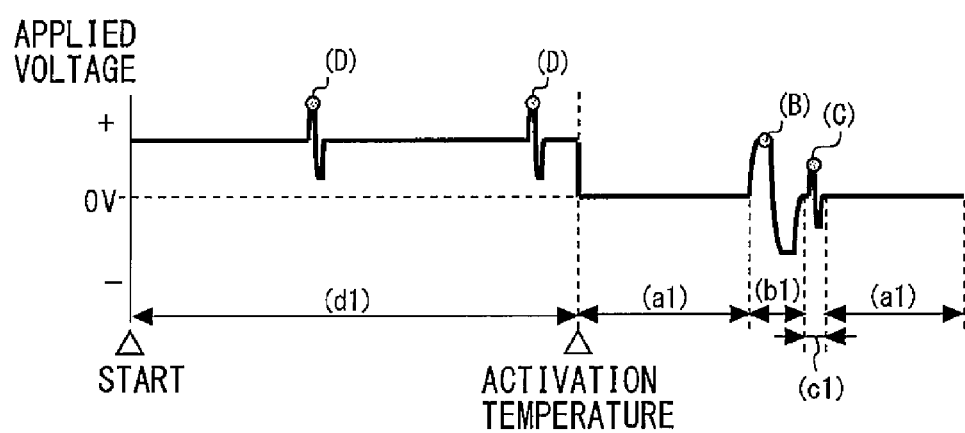
FIG. 13 is a diagram for describing another control example in Embodiment 5 of the present invention.

Further, a voltage that is applied for removing NOx in the pre-activation period is not limited to an alternating voltage. FIG. 13 is a timing chart for describing another example of NOx removal processing in the pre-activation period (d1) in Embodiment 5 of the present invention. According to this example, as shown in FIG. 13, a certain direct-current voltage for removing NOx is applied continuously during the pre-activation period (d1).

In this example, the alternating voltage for impedance detection in the pre-activation period (d1) is superimposed on a direct current for NOx removal, and the superimposed voltage is applied at fixed time intervals. The impedance can also be detected in this manner. The element temperature is detected in accordance with the detected impedance, and the control device 20 determines whether or not the sensor element has reached the activation temperature based on the element temperature that is detected. After the element temperature has reached the activation temperature, the control device 20 stops application of the direct-current voltage and starts the control for NOx concentration detection as described in any of Embodiments 1 to 4.

By continuously applying a direct-current voltage in this manner, a state in which decomposition of NOx at the detection electrode 32 is promoted can be maintained. Accordingly, similarly to the case of applying an alternating voltage for NOx removal, accumulation of NOx on the detection electrode 32 in the pre-activation period can be suppressed, and control for detecting the NOx concentration can be immediately started when the activation temperature is reached.

According to the present Embodiment 5 a case has been described in which control is performed to detect an element temperature by applying a voltage for impedance detection at fixed time intervals in the pre-activation period (d1). However, the present invention is not limited thereto, and a configuration may also be adopted that does not include such control for impedance detection. In such a case, whether or not the sensor element has reached the activation temperature may be determined based on a temperature detection value that is based on another sensor or based on an elapsed time period after startup or the like.

It is to be understood that even when the number, quantity, amount, range or other numerical attribute of an element is mentioned in the above description of the embodiments, the present invention is not limited to the mentioned numerical attribute unless it is expressly stated or theoretically defined. Further, structures and control processes and the like described in conjunction with the embodiments are not necessarily essential to the present invention unless expressly stated or theoretically defined.

DESCRIPTION OF REFERENCE NUMERALS 2 internal combustion engine
4 exhaust passage
8 urea injection valve
10 NOx catalyst
12 urea tank
14 NOx sensor
16 NOx sensor
20 control device
20 control device
30 solid electrolyte
32 detection electrode
34 reference electrode

The invention claimed is:

1. A NOx sensor control device that controls a first NOx sensor that is disposed upstream of a urea SCR catalyst and a second NOx sensor that is disposed downstream of the urea SCR catalyst in an exhaust passage of an internal combustion engine,
   wherein the first NOx sensor and the second NOx sensor each comprise a solid electrolyte and a pair of electrodes that are disposed so as to sandwich the solid electrolyte, and emits a sensor output that depends on a NOx concentration of a gas that is a detection object;
   the NOx sensor control device comprising:
   means for inducing, for a predetermined NOx adsorption period prior to detection of the sensor output, a state in which a voltage is not applied between the pair of electrodes or a state in which a potential difference between the pair of electrodes is less than a reference value;
   means for applying a voltage for sensor output detection between the pair of electrodes for a predetermined NOx detection period after the predetermined period elapses; and
   means for detecting a NOx concentration in accordance with the sensor output in the predetermined NOx detection period;
   wherein a length of the predetermined NOx adsorption period with respect to the first NOx sensor is shorter than a length of the predetermined NOx adsorption period with respect to the second NOx sensor.

2. The NOx sensor control device according to claim 1, wherein, after the predetermined NOx detection period elapses, the NOx sensor control device applies a voltage that is in an opposite direction to the voltage for sensor output detection and also is of a size that is less than or equal to the voltage for sensor output detection.

3. The NOx sensor control device according to claim 1, wherein a maximum value of the voltage for sensor output detection with respect to the first NOx sensor is less than a maximum value of the voltage for sensor output detection with respect to the second NOx sensor.

4. The NOx sensor control device according to claim 1, wherein a length of the predetermined NOx detection period with respect to the first NOx sensor is shorter than a length of the predetermined NOx detection period with respect to the second NOx sensor.

5. The NOx sensor control device according to claim 1, further comprising:
   means for applying, after the predetermined NOx detection period elapses, an alternating voltage for which a maximum value is smaller than a maximum value of the voltage for sensor output detection;

means for detecting an impedance of the solid electrolyte at a time that the small alternating voltage is applied; and means for detecting a temperature of a sensor element of the first NOx sensor and a temperature of a sensor element of the second NOx sensor in accordance with the impedance.

6. The NOx sensor control device according to claim 1, further comprising:

means for applying an alternating voltage for NOx removal between the pair of electrodes at fixed intervals to remove NOx that is present on the pair of electrodes during a period until a sensor element of the first NOx sensor reaches an activation temperature and also a sensor element of the second NOx sensor reaches an activation temperature; and means for applying, after application of the alternating voltage for NOx removal, an alternating voltage for which a maximum value is smaller than a maximum value of the alternating voltage for NOx removal;

means for detecting an impedance of the solid electrolyte at a time that the small alternating voltage is applied; and means for detecting a temperature of the sensor element of the first NOx sensor and a temperature of the sensor element of the second NOx sensor in accordance with the impedance.

7. A NOx sensor control device that controls a NOx sensor that is disposed in an exhaust passage of an internal combustion engine, wherein the NOx sensor comprises a solid electrolyte and a pair of electrodes that are disposed so as to sandwich the solid electrolyte, and emits a sensor output that depends on a NOx concentration of a gas that is a detection object;

the NOx sensor control device comprising:

means for alternately repeating a NOx adsorption state that is a state in which, for a predetermined NOx adsorption period, a voltage is not applied between the pair of electrodes or in which a potential difference between the pair of electrodes is less than a reference value, and a NOx detection state in which, for a predetermined NOx detection period after the predetermined NOx adsorption period elapses, a voltage for sensor output detection is applied between the pair of electrodes; and means for detecting a NOx concentration in accordance with the sensor output during the predetermined NOx detection period.

8. The NOx sensor control device according to claim 7, wherein, in a period after the predetermined NOx detection period elapses and before the predetermined NOx adsorption period starts, the NOx sensor control device applies a voltage that is in an opposite direction to the voltage for sensor output detection and is of a size that is less than or equal to the voltage for sensor output detection.

9. The NOx sensor control device according to claim 7, the NOx sensor control device being a control device that controls each of two NOx sensors that are a first NOx sensor disposed upstream of a urea SCR catalyst and a second NOx sensor disposed downstream of the urea SCR catalyst in the exhaust passage of the internal combustion engine, wherein a length of the predetermined NOx adsorption period with respect to the first NOx sensor is shorter than a length of the predetermined NOx adsorption period with respect to the second NOx sensor.

10. The NOx sensor control device according to claim 7, the NOx sensor control device being a control device that controls each of two NOx sensors that are a first NOx sensor disposed upstream of a urea SCR catalyst and a second NOx sensor disposed downstream of the urea SCR catalyst in the exhaust passage of the internal combustion engine, wherein a maximum value of the voltage for sensor output detection with respect to the first NOx sensor is less than a maximum value of the voltage for sensor output detection with respect to the second NOx sensor.

11. The NOx sensor control device according to claim 7, the NOx sensor control device being a control device that controls each of two NOx sensors that are a first NOx sensor disposed upstream of a urea SCR catalyst and a second NOx sensor disposed downstream of the urea SCR catalyst in the exhaust passage of the internal combustion engine, wherein a length of the predetermined NOx detection period with respect to the first NOx sensor is shorter than a length of the predetermined NOx detection period with respect to the second NOx sensor.

12. The NOx sensor control device according to claim 7, further comprising:

means for applying, in a period after the predetermined NOx detection period elapses and before the predetermined NOx adsorption period starts, an alternating voltage for which a maximum value is smaller than a maximum value of the voltage for sensor output detection;

means for detecting an impedance of the solid electrolyte at a time that the small alternating voltage is applied; and means for detecting a temperature of a sensor element of the NOx sensor in accordance with the impedance.

13. The NOx sensor control device according to claim 7, further comprising:

means for applying an alternating voltage for NOx removal between the pair of electrodes at fixed intervals to remove NOx that is present on the pair of electrodes during a period until a sensor element of the NOx sensor reaches an activation temperature;

means for applying, after application of the alternating voltage for NOx removal, an alternating voltage for which a maximum value is smaller than a maximum value of the alternating voltage for NOx removal;

means for detecting an impedance of the solid electrolyte at a time that the small alternating voltage is applied; and means for detecting a temperature of the sensor element in accordance with the impedance.

14. A NOx sensor control device that controls a NOx sensor that is disposed in an exhaust passage of an internal combustion engine, wherein the NOx sensor comprises a solid electrolyte and a pair of electrodes that are disposed so as to sandwich the solid electrolyte, and emits a sensor output that depends on a NOx concentration of a gas that is a detection object;

the NOx sensor control device comprising:

means for inducing, for a predetermined NOx adsorption period prior to detection of the sensor output, a state in which a voltage is not applied between the pair of electrodes or a state in which a potential difference between the pair of electrodes is less than a reference value;

means for applying a voltage for sensor output detection between the pair of electrodes for a predetermined NOx detection period after the predetermined NOx adsorption period elapses;

means for detecting a NOx concentration in accordance with the sensor output during the predetermined NOx detection period; and means for predicting NOx concentration of the gas that is the detection object based on an operating state of the internal combustion engine and modifying the predetermined NOx adsorption period based on the predicted NOx concentration so that the predetermined NOx adsorption period is longer when the predicted NOx concentration is lower than when the predicted NOx concentration is higher.

15. The NOx sensor control device according to claim 14, wherein, after the predetermined NOx detection period elapses, the NOx sensor control device applies a voltage that is in an opposite direction to the voltage for sensor output detection and is of a size that is less than or equal to the voltage for sensor output detection.

16. The NOx sensor control device according to claim 14, the NOx sensor control device being a control device that controls each of two NOx sensors that are a first NOx sensor disposed upstream of a urea SCR catalyst and a second NOx sensor disposed downstream of the urea SCR catalyst in the exhaust passage of the internal combustion engine, wherein a length of the predetermined NOx adsorption period with respect to the first NOx sensor is shorter than a length of the predetermined NOx adsorption period with respect to the second NOx sensor.

17. The NOx sensor control device according to claim 14, the NOx sensor control device being a control device that controls each of two NOx sensors that are a first NOx sensor disposed upstream of a urea SCR catalyst and a second NOx sensor disposed downstream of the urea SCR catalyst in the exhaust passage of the internal combustion engine, wherein a maximum value of the voltage for sensor output detection with respect to the first NOx sensor is less than a maximum value of the voltage for sensor output detection with respect to the second NOx sensor.

18. The NOx sensor control device according to claim 14, the NOx sensor control device being a control device that controls each of two NOx sensors that are a first NOx sensor disposed upstream of a urea SCR catalyst and a second NOx sensor disposed downstream of the urea SCR catalyst in the exhaust passage of the internal combustion engine, wherein a length of the predetermined NOx detection period with respect to the first NOx sensor is shorter than a length of the predetermined NOx detection period with respect to the second NOx sensor.

19. The NOx sensor control device according to claim 14, further comprising:

means for applying, after the predetermined NOx detection period elapses, an alternating voltage for which a maximum value is smaller than a maximum value of the voltage for sensor output detection;

means for detecting an impedance of the solid electrolyte at a time that the small alternating voltage is applied; and means for detecting a temperature of a sensor element of the NOx sensor in accordance with the impedance.

20. The NOx sensor control device according to claim 14, further comprising:

means for applying an alternating voltage for NOx removal between the pair of electrodes at fixed intervals to remove NOx that is present on the pair of electrodes during a period until a sensor element of the NOx sensor reaches an activation temperature;

means for applying, after application of the alternating voltage for NOx removal, an alternating voltage for which a maximum value is smaller than a maximum value of the alternating voltage for NOx removal;

means for detecting an impedance of the solid electrolyte at a time that the small alternating voltage is applied; and means for detecting a temperature of the sensor element in accordance with the impedance.

* * * * *